(12) United States Patent
von Borstel et al.

(10) Patent No.: US 6,403,565 B1
(45) Date of Patent: Jun. 11, 2002

(54) ANTIMUTAGENIC COMPOSITIONS FOR TREATMENT AND PREVENTION OF PHOTODAMAGE TO SKIN

(75) Inventors: Reid W. von Borstel, Potomac; Fedor Romantsev, Gaithersburg, both of MD (US)

(73) Assignee: Pro-Neuron, Inc., Gaithersburg, MD (US)

( * ) Notice: Subject to any disclaimer, the term of this patent is extended or adjusted under 35 U.S.C. 154(b) by 0 days.

(21) Appl. No.: 09/387,523

(22) Filed: Sep. 1, 1999

Related U.S. Application Data

(62) Division of application No. 08/963,831, filed on Nov. 4, 1997.

(51) Int. Cl.$^7$ ............................................. A61K 31/70
(52) U.S. Cl. ........................... 514/45; 514/46; 514/47; 514/48; 514/49; 514/50; 514/51
(58) Field of Search .............................. 514/45, 46, 47, 514/48, 49, 50, 51

(56) References Cited

U.S. PATENT DOCUMENTS

| | | | |
|---|---|---|---|
| 3,937,809 A | 2/1976 | Jacobi | |
| 4,537,776 A | 8/1985 | Cooper | |
| 4,557,934 A | 12/1985 | Cooper | |
| 5,246,708 A | 9/1993 | von Borstel et al. | |
| 5,250,290 A | 10/1993 | Giacomoni et al. | |
| 5,691,320 A | 11/1997 | von Borstel et al. | |
| 5,770,582 A | * 6/1998 | von Borstel et al. | |
| 6,020,320 A | 2/2000 | von Borstel et al. | |
| 6,020,322 A | 2/2000 | von Borstel et al. | |
| 6,060,459 A | 5/2000 | von Borstel et al. | .......... 514/45 |

FOREIGN PATENT DOCUMENTS

| | | |
|---|---|---|
| WO | 89/03838 | 5/1989 |
| WO | 94/13687 | 6/1994 |
| WO | 94/26761 | 11/1994 |
| WO | 95/01773 | 1/1995 |
| WO | 96/01115 | 1/1996 |
| WO | 00/11952 | 3/2000 |

OTHER PUBLICATIONS

Collins, Andrew R.S., et al., *J. Cell. Physiol*, 99: 125–138 (1979) "Repair and Survival after UV in Quiescent and Proliferating Microtus agrestis Cells: Different Rates of Incision and Different Dependence on DNA Precursor Supply."

Pashko, Laura L.,et al. *Carcinogenesis*, vol. 12, No. 11, pp. 2189–2192, 1991 "Inhibition of 12–O–tetradecanoylphorbol–13–acetate–oromoted skin tumor formation in mice by 15∀–fluoro–5–androsten–17–one and its reversal by deoxyribonucleosides."

Yew, Foch F.–H., et al, *Biochimica et Biophysica Acta*, 562 (1979) 240–251 "Ultraviolet–Induced DNA Excision Repair in Human Bandt Lymphocytes."

Yarosh, Daniel, et al, *Applied Genetics, Inc.*, p. 4227–4231, "Pyrimidine Dimer Removal Enhanced by DNA Repair Liposomes Reduces the Incidence of UV Skin Cancer in Mice." Improper Citation.

Musk, P., et al, *Mutation Research*, 227 (1989) 25–30, "Solar and UVC–induced mutation in human cells and inhibition by deoxynucleosides."

Bianchi, Vera, et al, *Mutation Research*, 146 (1985) 227–284, "Accuracy of UV–induced DNA repair in V79 cells in imbalance of deoxynucleotide pools."

Leder, Aya, et al, *Proc. Natl. Acad. Sci. USA*, vol. 87, pp. 9178–9182, Dec. 1990 Genetics, "v–Ha–ras transgene abrogates the initiation step in mouse skin tumorigenesis: Effects of phorbol esters and retinoic acid."

*Nature*, vol. 372, Dec. 1, 1994, p. 413–414, "DNA damage and melanogenesis."

Green, Michael H.L., et al, *Mutation Research, DNA Repair*, 315 (1994) 25–32, "Effect of deoxyribonucleosides on the hypersensitivity of human peripheral blood lymphocytes to UV–B and UV–C irradiation."

Kwon, Nyoun Soo, et al. *J. Exp. Med.*, The Rockefeller University Press, vol. 174, Oct. 1991, pp. 761–767, "Inhibition of tumor Cell Ribonucleotide Reductase by Macrophage–derived Nitric Oxide."

Newman, C.N., et al, *Mutation Research*, 200 (1988) 201–206, "Modulation of DNA precursor pools, DNA synthesis, and ultraviolet sensitivity of a repair–deficient CHO cell line by deoxycytidine."

Oliver, F. Javier, et al, *Biochem. J.*, (1996) 316, 421–425, "Regulation of the salvage pathway of deoxynucelotides synthesis in apoptosis induced by growth factor deprivation."

McKelvey, Valerie June, et al, *Leukemia Research*, vol. 12, No. 2, pp. 167–171, 1988, "Synergism Between U.V. and Thymidine Treatments in the Induction of Cytogenetic Damage in Wild–Type Friend Erythroleukaemia Cells."

* cited by examiner

*Primary Examiner*—James O. Wilson
(74) *Attorney, Agent, or Firm*—Nixon & Vanderhye

(57) ABSTRACT

A method of improving DNA repair and reducing DNA damage and for reducing mutation frequency in skin for the purpose of reducing consequences of exposure to solar or ultraviolet radiation is disclosed. The methods comprise administering to the skin a composition containing deoxyribonucleosides in concentrations sufficient to enhance DNA repair or reduce mutation frequency in a vehicle capable of delivering effective amounts of deoxyribonucleosides to the necessary skin cells.

67 Claims, No Drawings

ANTIMUTAGENIC COMPOSITIONS FOR TREATMENT AND PREVENTION OF PHOTODAMAGE TO SKIN

This is a divisional of application Ser. No. 08/963,831, filed Nov. 4, 1997, now pending, the entire content of which is hereby incorporated by reference in this application.

FIELD OF THE INVENTION

This invention relates generally to treatment and prevention of photodamage, genetic damage, and tumorigenesis in skin and other tissues caused by exposure to solar or ultraviolet radiation or other mutagens, comprising administration of deoxyribonucleosides or esters of deoxyribonucleosides to a mammal such as a human. These compounds are capable of reducing DNA damage, mutation frequency, and tumorigenesis when applied topically before, during, or after exposure to mutagenic radiation or chemical mutagens.

BACKGROUND OF THE INVENTION

Exposure of skin to ultraviolet (or ionizing) radiation damages DNA, which if unrepaired or improperly repaired, can lead to carcinogenesis as well as contribute to acceleration of the aging process. DNA damage and consequent genomic instability are defining characteristics of both carcinogenesis and biological aging. Patients with defective DNA repair capabilities in diseases like xeroderma pigmentosa display premature skin aging and a very high incidence of skin cancers (Robbins and Moshell, *J. Inv. Dermatol.*, 73:102–107, 1979) on sun-exposed areas of the skin. Pharmacological intervention in damage to skin due to solar or ultraviolet radiation has heretofore been largely restricted to agents like sunscreens or free-radical scavengers intended to prevent damage, or agents like retinoic acid or glycolic acid which are intended to remodel the surface of radiation-damaged skin without necessarily addressing the most fundamental mechanisms of cell or tissue damage and repair at the level of genomic integrity.

In practice, preventive measures like sunscreen use are not completely effective, and exposure to sunlight is not always anticipated. The incidence of skin cancers in the United States approaches 1,000,000 cases per year. Therefore, there exists a need for a therapeutic agent which will reduce the risk of development of skin cancer or other consequences of skin photodamage even when applied after exposure to sunlight has already occurred. Sunscreens and agents which induce or improve tanning are not useful in such situations, since they are only useful if applied prior to exposure to UV radiation. Moreover, there are situations wherein sunscreens and even endogenous melanin can actually enhance UV-induced DNA damage through photodynamic sensitization.

There have been several attempts to improve or accelerate DNA repair and to reduce the consequences of DNA damage in skin cells after damage has already occurred. The first major step in DNA repair is detection and excision of damaged portions of DNA. The viral enzyme T4 endonuclease V can accomplish this step with some forms of DNA damage. T4 endonuclease V, when packaged in epidermis-penetrating liposomes, has been shown to accelerate the rate of excision of pyrimidine dimers, the most common form of photolesion, in photodamaged skin of mice in vivo (Yarosh et al., *Cancer Res.* 52:4227–31, 1992). A bacterial extract has been reported to increase the rate of unscheduled DNA synthesis, which is often used as an index of DNA repair activity (Kludas and Heise, U.S. Pat. No. 4,464,362), in UV-exposed skin; however, this effect was not confirmed in a subsequent study (Natarajan et al., *Mutation Research* 206:47–54, 1988).

The key issue in DNA repair, however, is not necessarily the rate of lesion excision, but the fidelity of repair. Agents which accelerate the excision step of DNA repair can actually exacerbate damage if the cells are incapable of accurate repair synthesis at a rate that matches the rate of excision of damaged segments of DNA (Collins and Johnson, *J. Cell Physiol.* 99:125–137, 1979).

Deoxyribonucleosides or deoxyribonucleotides have been added to cells in culture with variable or divergent effects on DNA damage or mutagenesis in response to irradiation of the cells. In some cell types, e.g. lymphocytes, which have limited capabilities for de novo deoxyribonucleotide synthesis, exogenous deoxynucleosides are reported to improve cell survival after exposure to UV radiation (Yew and Johnson, *Biochim. Biophys. Acta*, 562:240–251, 1979; Green et al., *Mutation Research*, 350:239–246, 1996) or ionizing radiation (Petrovic et al., *Int. J. Radiat. Biol.*, 18:243, 1970); no significant improvement in survival was seen after addition of deoxyribonucleosides to UV-irradiated normal human fibroblasts (Green et al., *Mutation Research*, 350:239–246, 1996). A crucial point is that increasing cell survival after genomic damage caused by UV radiation or other mutagens is not necessarily desirable. The process of programmed cell death, or apoptosis, is integrated with cellular mechanisms for detecting DNA damage. Thus, genomic damage which by itself is not sufficient to cause cell death, can trigger apoptosis, an active cellular suicide process, so that the DNA damage in the cell is not perpetuated in subsequent cell generations, with tumorigenesis as a possible outcome as genomic damage accumulates. The mechanisms for detecting genomic damage and inducing apoptosis involve cell-cycle regulating proteins such as the tumor-suppressor protein p53. Therefore, agents which promote cell survival (e.g. by inhibiting apoptosis) after irradiation are not necessarily anticarcinogenic, and may actually enhance mutation frequency and risk of malignant transformation by permitting survival of damaged cells that would otherwise be eliminated by apoptosis. A significant illustration of this principle is the demonstration that embryonic p53 knockout mice exposed to ionizing radiation in utero have a higher survival rate (live birth) than wild-type controls, but also have a much higher frequency of congenital defects (Norimura et al., *Nature Medicine*, 2:577–580).

In studies where the effect of exogenous deoxyribonucleosides on mutation frequency in UV-irradiated cells has been explicitly studied, variable results have been obtained. Bianchi and Celotti (*Mutation Research* 146:277–284, 1985) reported that thymidine or deoxycytidine at high concentrations increased the mutation frequency in UV-irradiated V79 Chinese hamster cells; no reduction in mutation frequency was observed at any concentrations of added nucleosides. Musk et al. (*Mutation Research* 227:25–30, 1989) reported that a mixture of deoxyribonucleosides which included excess deoxycytidine relative to the other nucleosides, reduced the mutation frequency in response to UV-C (254 nm) irradiation in MM96L melanoma cells, a cell line with a known constitutive excess of purine deoxyribonucleotides. In the same study, exogenous deoxyribonucleosides had no effect on mutation frequency in another neoplastic cell line, human HeLa cells, after exposure to UV-C radiation. It is important to note that UV-C radiation is not a component of solar radiation at the surface of the earth, since it is blocked effectively by the atmosphere (Pathak, 1974, in *Sunlight and Man,* ed. by T. B. Fitzpatrick, University of Tokyo Press, Tokyo, Japan, p. 815). The effect of deoxyribonucleosides on mutation frequency in cells exposed to solar radiation or UV radiation at wavelengths that are present in solar radiation was not tested, and the authors explicitly conclude their discussion with the statement " . . . the lower [mutation] frequency in sun-[irradiated] compared with UVC-irradiated MM96L cells suggests that sunlight either does not perturb the deoxynucleoside pools or it induces a cellular response that is insensitive to nucleoside levels."

In addition to agents which inhibit apoptosis or improve DNA repair sufficiently to permit cell survival but not necessarily for correction of potentially tumorigenic mutations, growth factors in general (including those that are involved in normal wound healing responses like TGF-β or PDGF) act as tumor promoters.

U.S. Pat. No. 5,246,708 discloses the methods and compositions involving the use of mixtures of deoxyribonucleosides for promotion of the healing of wounds, ulcers, and burns, including those caused by ultraviolet or solar radiation.

Acyl derivatives of deoxyribonucleosides have been taught as delivery molecules for promoting entry of deoxyribonucleosides into the skin, as disclosed in U.S. patent application Ser. No. 08/466,379, filed Jun. 6, 1995, now U.S. Pat. No. 6,297,222. It is disclosed that acyl derivatives of deoxyribonucleosides can improve cellular repair and cell survival after damage to skin caused by radiation.

Oligodeoxyribonucleotides have been proposed as melanogenic stimuli, based on the idea that DNA damage, or excision products of DNA damage, might be cellular signals for increasing melanin production in the skin to help protect against subsequent damage. Gilchrest et al. (U.S. Pat. No. 5,470,577; WO Application Ser. No. 95/01773) proposed that exogenous DNA photodamage products may stimulate melanogenesis without actual damage to cellular DNA as a necessary intermediate step. The stated intention was to mimic the presence of cyclobutane pyrimidine dimers or other DNA photodamage products in order to provide the cell with false DNA damage signals that might trigger induction of melanogenesis in the absence of actual DNA damage. Treatment of melanoma cells in vitro and guinea pig skin in vivo with thymidine dinucleotide resulted in increases in melanin production. The authors stated that they believed that DNA fragments entered the cells, and even their nuclei, intact. They proposed that sunless tanning accomplished over a period of weeks by topical administration of oligodeoxyribonucleotides, especially thymidine dinucleotide, could protect skin by inducing melanin synthesis, with consequent reduction of passage of UV radiation into and through the skin.

Wiskemann (1974; in Sunlight and Man, ed. by T. B. Fizpatrick, University of Tokyo Press, Tokyo, Japan, p. 51) reported that systemic (intraperitoneal) administration the deoxyribonucleoside thymidine or the ribonucleosides and congeners adenosine, cyclic-AMP, uridine, cytidine increased the period of latency for extravasation of systemically administered Evan's Blue dye in the skin in the first few hours after UV exposure, indicating a reduction in acute UV-induced edema. In this system, DNA administered after irradiation had no effect on extravasation of dye. The author also explicitly states that nucleobases incorporated into ointments do not penetrate the horny layer (the stratum corneum, the outer layer of enucleated keratinocytes comprising the main moisture barrier of skin) of human epidermis.

OBJECTS OF THE INVENTION

It is an object of the invention to provide compositions and methods for reducing mutation frequency, photoaging, and tumorigenesis in skin, thereby attenuating consequences of exposure to solar and ultraviolet radiation and to other mutagens including endogenous oxidants.

It is an object of the invention to provide a composition that enhances DNA repair and prevents consequences of mutagenic radiation even when administered after damage or exposure to radiation or other mutagens has already occurred.

It is a primary object of this invention to provide compositions and methods for effectively preventing or treating consequences of exposure of the skin to solar and ultraviolet radiation and other environmental mutagens.

It is a further object of the invention to provide compositions and methods for improving the activity of chemical sunscreens.

It is a further object of the invention to provide compositions and methods for reducing deleterious effects of sunscreens and other compounds, exogenous and endogenous, which act as photosensitizing or photodynamic enhancers of UV-induced damage to skin.

It is a further object of the invention to provide compositions and methods for reducing some consequences of inflammatory skin and mucosal conditions, including psoriasis, dermatitis and inflammatory bowel disease.

SUMMARY OF THE INVENTION

The subject invention involves methods and compositions for improving DNA repair (or genomic fidelity) and reducing photodamage in skin exposed to ultraviolet radiation, ionizing radiation, or chemical mutagens by topical administration of compositions containing effective amounts of a source of deoxyribonucleosides. The compositions are capable of delivering deoxyribonucleosides to the necessary target cells. Such compositions are applied to the skin before, during or after exposure to solar, ultraviolet, or ionizing radiation, or chemical mutagens including but not limited to endogenous or exogenous sources of free radicals or nitric oxide. Treatment with compositions of the invention improves the net fidelity of DNA repair and thereby reduces mutation frequency and the risk of tumorigenesis in response to solar or ultraviolet radiation or other mutagens.

The invention provides methods and compositions for delivering deoxyribonucleosides to skin cells in concentrations sufficient to support and improve repair of damaged DNA and to reduce deleterious consequences of exposure of skin to radiation or chemical mutagens.

The deoxyribonucleosides are administered either as free deoxyribonucleosides, or as derivatives thereof which are converted to deoxyribonucleosides after application to the skin. Such derivatives include deoxyribonucleotides, oligonucleotides, DNA itself, and acyl derivatives of deoxyribonucleosides or other derivatives of deoxyribonucleosides which are converted to free deoxyribonucleosides by endogenous enzymes.

Methods and compositions of the invention also improve activity and reduce side effects of other agents used on skin for prophylactic, therapeutic, or cosmetic purposes, including but not limited to sunscreens, retinoids, alpha-hydroxy acids, methylxanthines, and DNA repair enzymes.

The invention also relates to compositions and methods for reducing deleterious consequences (e.g. cellular damage, especially to DNA, which can result in increased likelihood of mutations or other potentially carcinogenic damage to the genome) of endogenous and exogenous photochemically-active compounds or chromophores which act as photosensitizers or photodynamic enhancers of DNA damage caused by solar or ultraviolet radiation.

The invention, as well as other objects, features and advantages thereof will be understood more clearly and fully from the following detailed description, when read with reference to the accompanying results of the experiments discussed in the examples below.

DETAILED DESCRIPTION OF THE INVENTION

DNA damage and repair is involved in the development of skin cancer and photoaging. The subject invention provides compounds which successfully improve the net fidelity of DNA repair. The subject invention will have important consequences in health care and will improve the cosmetic appearance of skin.

A. Definitions

The term "deoxyribonucleoside" refers to any one of the four principle nucleoside constituents of DNA: deoxyadenosine, deoxycytidine, deoxyguanosine, and thymidine. The term "ribonucleoside" refers to any one of the four major nucleoside constituents of RNA: adenosine, cytidine, guanosine, and uridine.

The term "acyl derivative of a deoxyribonucleoside" refers to deoxyribonucleosides bearing acyl substituents derived from carboxylic acids (which modify the pharmacokinetics and bioavailability of the free deoxyribonucleosides), as disclosed in U.S. Pat. No. 6,297,222, hereby incorporated by reference in its entirety.

The term "source of at least one deoxyribonucleoside" or "deoxyribonucleoside source" in the context of the subject invention refers to deoxyribonucleosides themselves or derivatives of deoxyribonucleosides which can be converted to deoxyribonucleosides by endogenous enzymes, especially esterases. Examples include acyl derivatives of deoxyribonucleosides (carboxylic acid esters), deoxyribonucleotides (phosphate esters), or oligodeoxyribonucleotides (phosphate diesters). Since esterase activity (involving various enzymes capable of cleaving carboxylic acid esters and phosphate esters) is ubiquitous in mammalian tissues including skin, these esters of deoxyribonucleosides a re converted to deoxyribonucleosides when applied to skin. Similarly, a "source of at least one ribonucleoside" refers to a ribonucleoside or ribonucleoside ester, including a ribonucleotide, an oligoribonucleotide, or an acyl derivative of a ribonucleoside.

The term "ester of a deoxyribonucleoside" (or deoxyribonucleoside ester) refers to either an acyl derivative of deoxyribonucleosides as described above or to a phosphate ester of a deoxyribonucleoside (or deoxyribonucleosides), e.g. deoxyribonucleotides, oligodeoxyribonucleotides, or polydeoxyribonucleotides.

The term "photosensitization" in the context of the subject invention refers to the process whereby light-absorbing (UV or visible light) molecules directly transfer the energy of an excited state, generally a triplet state, to a target molecule, resulting in damage to DNA and other cellular structures. The target molecule can be DNA itself or another target which results in damage to DNA, e.g. membranes components of lysosomes, which contain deoxyribonuclease.

The term "photodynamic sensitization" herein refers to the process whereby UV-absorbing molecules generate free radical species or other diffusible reactive intermediates as a result of excitation by UV or visible radiation.

The term "sunscreen agents" refers to a UV-absorbing chemicals that are intended to be used in sunscreen products as active ingredients for reducing exposure of the skin to the UV component of solar radiation. Examples of sunscreen agents currently used as such in commercial products include avobenzone (t-butyl dimethoxydibenzoylmethane), oxybenzone (benzophenone-3), dioxybenzone (benzophenone-8), sulisobenzone (benzophenone-4; 2-hydroxy-4-methoxybenzophenone-5-sulfonic acid), octocrylene (2-ethylhexyl-2-cyano-3,3-diphenylacrylate), octyl methoxycinnamate (2-ethylhexyl p-methoxycinnamate), octyl salicylate (2-ethylhexylsalicylate), homosalate (homomenthyl salicylate), trolamine salicylate (triethanolamine salicylate), phenylbenzimidazole sulfonic acid, PABA (para-aminobenzoic acid), roxadimate (ethyl 4-bis hydroxypropyl aminobenzoate), lisadimate (glyceryl PABA), Padimate 0 (octyldimethyl PABA), menthyl anthranilate, and Parsol 1789 (butyl methoxydibenzoyl methane).

The term "energy scavenger" refers to a compound which absorbs energy from the excited states of sunscreen agents or endogenous photosensitizing or photodynamic enhancers of DNA damage, reducing damage to target biological molecules like DNA. In this context, energy scavengers should be nontoxic at effective concentrations and should yield a net reduction in damage to DNA when present during UV irradiation in the presence of a photosensitizer or photodynamic enhancer of DNA damage. In the context of this invention, "energy scavengers" refer particularly to compounds with lowest triplet states with energies less than or equal to those of the nucleobase constituents of genomic DNA. The primary quality of energy scavengers of the invention is that, by virtue of photochemical energy state properties, or mass action (concentration), they prevent damage to genomic DNA that would otherwise occur due to energy transfer for excited chromophores, whether endogenous (e.g. melanin) or exogenous (e.g. sunscreens). Energy scavengers with photochemical properties similar to those of structural constituents of DNA are advantageous, and include sources of at least one deoxyribonculeoside or ribonucleoside, like a deoxyribonucleoside, an acyl deoxyribonucleoside, a deoxyribonucleotide, an oligodeoxyribonucleotide, a ribonucleoside, a ribonucleotide, an oligoribonucleotide, and an acyl ribonucleoside.

The term "deleterious consequences" as used herein refers to cellular damage in a mammal caused by a mutagen, especially damage to the genome, resulting in an increased chance of developing skin cancer or other skin lesions like solar lentigines, actinic keratoses, or other signs of photoaging like skin wrinkles or "age spots". Mutagens capable of causing such deleterious consequences include solar radiation, ultraviolet radiation, ionizing radiation, free radicals (whether produced as a result of irradiation of a photochemically active chromophore or from some other source, including normal metabolic processes), nitric oxide, and environmental mutagens.

B. Compounds of the Invention

The compounds of the invention are primarily the major deoxyribonucleoside constituents of DNA: deoxyadenosine, deoxycytidine, deoxyguanosine, and thymidine. The invention also includes the use of effective amounts of precursors of these deoxyribonucleosides, e.g. oligodeoxyribonucleotides, DNA, deoxyribonucleotides and acyl derivatives of deoxyribonucleosides, and, particularly for minimization of effects of photodynamic sensitizers and photosensitizing agents on DNA, ribonucleosides and their congeners, e.g. oligoribonucleotides, ribonucleotides, and acyl derivatives of ribonucleosides.

While not wishing to be bound by a theory, it is believed that the active agents of the invention that pass into cells are the deoxyribonucleosides or acyl derivatives of deoxyribonucleosides, since the anionic phosphate moiety on deoxyribonucleotides or oligodeoxyribonucleotides impedes passage across cell membranes. Phosphorylated deoxyribonucleoside precursors are converted to free deoxyribonucleosides by enzymatic and nonenzymatic degradation before or after application to the skin, prior to their entry into cells.

The deoxyribonucleosides are produced by any of several methods. They are produced by degradation of DNA from biological sources, e.g. fish sperm, by chemical synthesis, or by fermentation technology.

Also encompassed by the invention are pharmaceutically acceptable salts of the above-noted compounds.

C. Compositions of the Invention

The invention includes pharmaceutical compositions for improving the net fidelity of DNA repair and for protecting the skin against mutagens. The composition comprises 1) an effective amount of a source of one or more deoxyribonucleosides, and optionally 2) an effective amount of a pharmaceutically acceptable topical carrier capable of delivering the deoxyribonucleosides or their precursors to appropriate target cells in the skin under in vivo conditions.

While individual deoxyribonucleosides, especially deoxycytidine (see Example 7) have some activity in attenuating UV-induced tumorigenesis, two or more deoxyribonucleosides, or preferably all four, are typically included in a formulation of the invention. Encompassed by the invention are compositions containing deoxyadenosine, deoxycytidine, deoxyguanosine, or thymidine, either as single agents, or in all possible combinations of two, three, or all four of these compounds. Compositions containing deoxycytidine are particularly advantageous. The concentrations of individual deoxyribonucleosides in compositions encompassed by the invention, whether present individually or in combination with other deoxyribonucleosides or deoxyribonucleoside precursors (such as deoxyribonucleoside esters), and normalized to the amount of free nucleoside or nucleoside moiety in the case of deoxyribonucleoside phosphates or oligonucleotides or prodrugs like acylated deoxyribonucleoside derivatives, range from 0.1 to 10 mg/ml, advantageously 1 to 5 mg/ml.

In order to permit access of the deoxyribonucleosides and related compounds of the invention to deeper-lying skin cells, vehicles which improve their penetration through the outer layers of the skin, e.g. the stratum corneum, are useful. Vehicle constituents which improve the penetration of compounds of the invention into the skin include but are not limited to: ethanol, isopropanol, azone (1-dodecylazacycloheptan-2-one), oleic acid, linoleic acid, propylene glycol, hypertonic concentrations of glycerol, lactic acid, glycolic acid, citric acid, and malic acid.

In addition to promoting absorption of agents into the skin, use of topical alpha-hydroxy acids (AHA), e.g. lactic acid and glycolic acid, can affect the ability of the skin to reduce the penetration of ultraviolet light into the vulnerable basal layers of the epidermis. Thus, there is also an increased need for agents which reduce the consequences of exposure to solar or ultraviolet radiation in people using AHA's, e.g. for promoting exfoliation of epidermal cells. Since penetration of UV-absorbing sunscreen agents into the skin is undesirable because of possible photosensitization and photodynamic enhancement of UV-induced damage to cells, the compounds of the invention are uniquely suitable for combination with AHA's, either in the same formulation or a separate one, for improving skin resistance to damaging effects of solar or ultraviolet radiation.

One embodiment of the invention is a hydrogel formulation, comprising an aqueous or aqueous-alcoholic medium and a gelling agent, and a deoxyribonucleoside source. Suitable gelling agents include but are not limited to methylcellulose, carboxymethylcellulose, hydroxypropylmethylcellulose, carbomer (carbopol), hypan, polyacrylate, and glycerol polyacrylate.

Liposomes are microscopic lipid vesicles which can contain pharmacologically active agents either enclosed in the aqueous space within the vesicle or in the lipid membrane itself, depending on the lipophilicity of the agent. Liposomes are capable of delivering a pharmacologic agent through the stratum corneum into deeper layers of the skin, and are therefore suitable vehicles for compounds and compositions of the invention.

Niosomes are lipid vesicles similar to liposomes with membranes consisting largely of non-ionic lipids, some forms of which are effective for transporting compounds across the stratum corneum.

In one embodiment of the invention, lipophilic acyl derivatives of deoxyribonucleosides, e.g. oleic or palmitic acid esters of deoxyribonucleosides are incorporated into membranes of niosome or liposome membranes, in addition to or instead of being enclosed within the vesicular membranes.

Other agents which are advantageous for incorporation into a composition of the invention include corticosteroids, especially hydrocortisone in concentrations of 0.05 to 1%, other anti-inflammatory corticosteroids at therapeutically effective concentrations, topical anesthetics including but not limited to benzocaine, lidocaine, and benzyl alcohol, aloe vera and aloe barbadensis, retinoids, antioxidants like Vitamins C and E, flavins, polyphenols (e.g. extracted from green tea or black tea), allantoin, liposomal DNA repair enzymes, antibacterial agents (e.g. quaternary ammonium compounds, bacitracin, neomycin, polymyxin), zinc salts, and methylxanthines. All of these listed agents have some utility in treating or attenuating various aspects of skin injury or discomfort caused by ultraviolet radiation or inflammatory skin conditions, and are therefore complementary to the unique actions of the deoxyribonucleosides of the invention.

Benzyl alcohol, which is known to have anesthetic and preservative properties, has the unexpected effect of improving aqueous solubility of the relatively insoluble purine deoxyribonucleosides, deoxyadenosine and deoxyguanosine; preferred concentrations of benzyl alcohol in topical formulations of deoxyribonucleosides are 0.5 to 5%. This is very important in permitting high concentrations of the deoxyribonucleosides of the invention to be stably incorporated into aqueous vehicles.

Sunscreens

The compounds of the invention are advantageously incorporated into the same formulation as a UV-absorbing chemical sunscreen agent such as: avobenzone (t-butyl dimethoxydibenzoylmethane), oxybenzone (benzophenone-3), dioxybenzone (benzophenone-8), sulisobenzone (benzophenone-4; 2-hydroxy-4-methoxybenzophenone-5-sulfonic acid), octocrylene (2-ethylhexyl-2-cyano-3,3-diphenylacrylate), octyl methoxycinnamate (2-ethylhexyl p-methoxycinnamate), octyl salicylate(2-ethylhexylsalicylate), homosalate (homomenthyl salicylate), trolamine salicylate (triethanolamine salicylate), phenylbenzimidazole sulfonic acid, PABA (para-aminobenzoic acid), roxadimate (ethyl 4-bis hydroxypropyl aminobenzoate), lisadimate (glyceryl PABA), Padimate O (octyldimethyl PABA), menthyl anthranilate, or Parsol 1789 (butyl methoxydibenzoylmethane).

Alternatively, the compounds of the invention are formulated in a base which is suitable for application to the skin prior to, or after, application of a sunscreen. This embodiment of the invention permits the benefits of deoxyribonucleosides, in reducing consequences of UV damage and in attenuating photodynamic enhancement of cellular damage caused by sunscreen agents themselves, to be obtained in conjunction with use of a wide variety of commercial sunscreen products.

D. Therapeutic Uses of the Compounds and Compositions of the Invention

Reduction of Deleterious Consequences of Exposure of Skin to Ultraviolet or Solar Radiation The compounds and composition of the invention, when applied or administered before, during, or after exposure of the skin of a mammal to mutagenic radiation, have the unexpected activity of improving the net fidelity DNA repair, thereby reducing mutation frequency, photoaging, and the chance of developing skin cancers.

DNA repair proceeds by several steps. A chemical lesion in DNA, which can be caused by ultraviolet radiation, ionizing radiation, free radicals, or chemical mutagens, is detected by the DNA repair system. A segment of nucleotides including the damaged region is excised, generally along with a number of surrounding nucleotides. The excised strand is then resynthesized from free deoxyribonucleotides, using the intact DNA strand as a template.

It is generally believed that improvement of repair of DNA in skin cells (e.g. keratinocytes, melanocytes, fibroblasts) would require alteration in the activity of enzymes or other proteins involved in the detection and excision of DNA lesions. Thus, there have been attempts to improve DNA repair in skin by delivering DNA repair enzymes via topically-applied liposomes (U.S. patents (Yarosh et al., *Cancer Res.* 52:4227–31, 1992).

Far more important than the initial rate of excision of lesions is the fidelity or accuracy of repair. Agents which accelerate the excision step of DNA repair can actually exacerbate damage if the cells are incapable of accurate repair synthesis at a rate that matches the rate of excision of damaged segments of DNA (Collins and Johnson, *J. Cell Physiol.* 99:125–137, 1979).

Compounds and compositions of the invention, when applied to skin before, during or after exposure to solar or ultraviolet radiation or other environmental mutagens, reduces the mutation frequency otherwise induced by the mutagen (Example 1). This reduces the damage to cells caused by the mutagen, and reduces the chance of development of skin cancers, as shown in Examples 2 and 7. The effect on genomic fidelity is in principle mediated by actual improvement in the fidelity of repair in an individual cell or by improvement of the elimination of cells with irreparable DNA damage. Either mechanism results in a net improvement in genomic fidelity in skin exposed to mutagens.

The compounds of the invention have unanticipated benefits when used in combination with other agents known to be useful in various aspects of skin care, including but not limited to sunscreens, methylxanthines, retinoids, DNA repair enzymes, exfoliants, and protease inhibitors, corticosteroids and nonsteroidal anti-inflammatory agents.

The compounds and compositions of the invention, when applied soon enough, e.g. within about 3 days after exposure to ultraviolet or solar radiation, improve the repair of cellular and macromolecular damage and improve net genomic fidelity, thereby reducing the chance of development and severity of macroscopically visible deleterious consequences of such exposure, including but not limited to photoaging, sunburn symptoms, actinic keratoses, solar lentigines, "age spots", and skin cancer. The compounds and compositions of the invention are also optionally applied before or during exposure to solar or ultraviolet radiation to shorten the time gap between damage and onset of repair enhancement by the compounds of the invention.

Treatment of skin with compounds and compositions of the invention results in a reduced chance of development of skin cancers and other deleterious consequences of exposure to solar or UV radiation like photaging even when the compounds of the invention are applied even after irradiation, e.g. after unintended exposure to potentially-damaging doses of solar radiation. This type of activity is not shared by conventional sunscreens or agents which might act by enhancing melanogenesis, which are useful only if applied before irradiation.

Improvement of Sunscreen Activity and Attenuation of Photodynamic Enhancement of UV Damage by Sunscreens Sunscreens are typically designed and tested on the basis of prevention of sunlight-induced erythema. While erythema and its attenuation by sunscreens is an important short-term effect, reduction of erythema and inflammation by sunscreens does not necessarily mean that they produce a proportionate protection of DNA (or prevention of skin cancers and some features of photoaging secondary to DNA damage). Sunscreens are certainly useful in preventing some manifestations of photoaging and UV-related carcinogenesis, but do not provide complete protection, and in some situations may actually exacerbate photoinjury by acting as photodynamic sensitizers (see Example 3).

Chemical sunscreens are intended to act by absorbing photons at mutagenic (or erythmogenic) wavelengths, thus producing a short-lived excited singlet state; return to the ground state is accompanied by photon emission at longer wavelengths that are supposed to be less harmful than the incident radiation. Photon emission during the rapid return of a molecule from an excited singlet state to a ground state is known as "fluorescence". However, sunscreens or other exogenous or endogenous UV-absorbing molecules can also be excited to longer-lived triplet states which can facilitate further reactions (the energy-emission that occurs during return of a molecule from an excited triplet state to a ground state is known as "phosphorescence", and typically occurs over a much longer time span than fluorescence). The consequence is that some UV-absorbing agents, especially those with a lowest triplet state that has a higher energy level than the lowest triplet state of genomic DNA constituents, can absorb photons and actually exacerbate damage to DNA by direct or indirect energy transfer (e.g. from a triplet excited state) rather than by simple fluorescence, or photon emission at harmless wavelengths.

Benzophenone, a close structural analog of oxybenzone, increases the yield of strand breaks and pyrimidine dimers in UV-irradiated DNA, and is known to produce free radicals upon irradiation with UV light (Charlier et al., *Photochemistry and Photobiology*, 15:527–536, 1972). The results presented in Examples 3, 4, 5 and 6 indicate that a similar phenomenon also occurs with approved sunscreen ingredients, and that the deoxyribonucleosides of the invention attenuate this deleterious consequence of sunscreen use.

When present in concentrations sufficient to block access of UV radiation to cells, sunscreen agents are protective.

However, if present in very low concentrations, insufficient to adequately block UV transmission, photon-absorbing agents, including common sunscreen ingredients, can operate as energy-transfer molecules, efficiently trapping UV energy and transferring it to cell components, either directly (photosensitization) or by catalyzing formation of reactive oxygen radicals (photodynamic sensitization). Thus, low concentrations of oxybenzone, for example, enhance DNA damage induced by ultraviolet radiation, whereas higher concentrations, sufficient to block UV access to the cells or their immediate microenvironment altogether, protect against DNA damage (see Example 3).

The expected activity in vivo is that an oxybenzone-containing sunscreen would protect cells from damage if present in a layer sufficient to block access of light to the target cells altogether. However, at lower concentrations, insufficient to prevent penetration of UV radiation to target cells, and especially if some oxybenzone has been absorbed into the critical cell layers, either via passage through the stratum corneum or through hair follicles, there may be potentiation of damage to DNA in vivo. In mice treated topically with commercial sunscreen containing oxybenzone, effects consistent with this hypothesis are in fact observed after exposure to UV (see Example 6). Classes of sunscreens other than benzophenone derivatives also exacerbate UV-induced damage to DNA when present at low concentrations during irradiation.

A strain of transgenic mice (v-HA-ras transgenic TG.AC mice) which is very susceptible to a variety of carcinogens, including UV radiation has been developed recently (Leder et al., *Proc. Nat. Acad. Sci. USA*, 87:9178–9182, 1990). In response to a relatively small exposure to UV radiation, these mice reliably develop cutaneous papillomas within a few weeks. When a circular patch of commercial sunscreen is applied to the back of such a mouse, the center of the protected region does in fact have lower incidence of UV-induced papillomas than the unprotected side, but often, along the margin of the applied sunscreen, there is a very high incidence (sometimes higher than in unprotected areas) of papillomas (See Example 6). A layer of sunscreen sufficient to block UV access to target cells is protective, but low concentrations, e.g. at the margin of a patch of sunscreen) can act as photosensitizers increasing the incidence of a UV-induced skin cancer beyond that seen in completely "unprotected" skin. Exposure of relevant skin cells to low photosensitizing (rather than protective) concentrations of sunscreens clearly must occur during ordinary usage, e.g. at the margin of an applied patch, or as a protective layer is washed or worn off.

A benefit of deoxyribonucleosides or related compounds added to conventional sunscreen formulations (or other cosmetics containing sunscreens), beyond the support of DNA repair, is to synergize with conventional sunscreen compounds by acting as energy scavengers which trap energy emitted by (or radicals produced by) sunscreen agents that is chemically similar to the cellular target, DNA. Exogenous deoxyribonucleosides (in addition to their direct absorbance of UV energy) serve as "decoys" for energy captured by sunscreen agents or other photosensitizers that would otherwise be transferred to cellular targets, including DNA. Thus, deoxyribonucleosides provide a dose-dependent reduction in damage caused to cellular DNA by UV radiation in the presence of low concentrations of photosensitizing agents like oxybenzone or other sunscreen agents (Example 4).

A defining characteristic of suitable energy scavenging agents is that their lowest triplet energy state is equal to or lower than that of DNA constituents in situ. Because of the similarity of physicochemical properties of deoxyribonucleosides (or deoxyribonucleotides, acyl deoxyribonucleosides, or oligodeoxyribonucleotides) and genomic DNA, the compounds of the invention are particularly suitable as energy-scavenging agents to protect genomic DNA from damage due to energy transfer from photosensitizers or photodynamic sensitizers. In this embodiment, ribonucleosides, ribonucleotides, oligoribonucleotides and acyl derivatives of ribonucleosides are within the scope of the invention. Appropriate concentrations of such scavengers in a composition for topical application range from 0.1 to 100 milligrams per milliliter (normalized to the amount of free nucleoside present in the case of nucleotides or oligonucleotides or acyl derivatives of nucleosides). Advantageously, such scavengers are present in concentrations ranging from 0.1 to 20 mg/ml or especially 1 to 5 mg/ml.

The problem of photodynamic enhancement of damage to DNA extends beyond sunscreens. Other compounds including endogenous molecules in the skin, can absorb UV radiation at wavelengths that do not necessarily directly damage DNA significantly, and transfer that energy to cellular targets including DNA, or generate free radicals that damage cellular DNA. Examples of endogenous photosensitizing or photodynamically active skin constituents (photochemically active chromophores) include but are not limited to porphyrins, tryptophan, riboflavin, and melanin. Exogenous photodynamically active compounds include psoralens, which are present in some perfume oils (bergamot), and which are in fact used to enhance sunlight-induced tanning and UV phototherapy of psoriasis through exacerbation of cellular injury. Many therapeutic drugs or their metabolites are photochemically active chromophores which can produce skin adverse reactions when a patient is exposed to solar, visible, or ultraviolet radiation. Pigments and other light-absorbing constituents of cosmetics are also photochemically active chromophores which can exacerbate cellular photodamage.

The deoxyribonucleosides and related compounds of the invention (e.g. deoxyribonucleotides, oligonucleotides, or DNA itself) are useful for attenuating cellular damage caused by excited light-absorbing molecules, including exogenous photochemically active chromophores like sunscreens and cosmetic pigments, and also from endogenous chromophores like tryptophan, porphyrins, urocanic acid and melanin.

Furthermore, since the photodynamic enhancement of DNA damage caused by benzophenone derivatives is in part mediated by production of free radicals (Charlier et al., *Photochemistry and Photobiology*, 15:527–536, 1972), compounds and compositions of the invention are useful for protecting the skin and mucosa from free radical damage, whether or not the free radicals (e.g. hydroxyl radicals, peroxide radicals, or lipoperoxide radicals) are initiated or produced by photodynamic phenomena. Examples 3,4,5 and 6 provide evidence that the deoxyribonucleosides of the invention protect against DNA caused by free radicals.

The deoxyribonucleosides and related compounds of the invention are advantageously incorporated into the same formulation as chemical sunscreen agents, which include but are not limited to: avobenzone (t-butyl dimethoxydibenzoylmethane), oxybenzone (benzophenone-3), dioxybenzone (benzophenone-8), sulisobenzone (benzophenone-4), octocrylene (2-ethylhexyl-2-cyano-3,3-diphenylacrylate), octyl methoxycinnamate (2-ethylhexyl p-methoxycinnamate), octyl salicylate (2-ethylhexylsalicylate), homosalate (homomenthyl salicylate), trolamine salicylate (triethanolamine salicylate), phenylbenzimidazole sulfonic acid, PABA (para-aminobenzoic acid), roxadimate (ethyl 4-bis hydroxypropyl aminobenzoate), lisadimate (glyceryl PABA), Padimate O (octyldimethyl PABA), menthyl anthranilate, or Parsol 1789 (butyl methoxydibenzoylmethane). Such sunscreen agents are present in formulations at concentrations that are in accord with regulatory guidelines and standard use.

Similarly, in another embodiment of the invention, compounds of the invention are incorporated into cosmetics containing photochemically active chromophores to minimize deleterious consequences of combined exposure of skin to solar or ultraviolet radiation and such cosmetic ingredients.

Alternatively, the compounds of the invention are applied to the skin in a separate composition, e.g. a spray, lotion, roll-on, stick, or gel, before or after a sunscreen product or cosmetic is applied.

Methylxanthines

Methylxanthines, such as caffeine, theophylline, aminophylline or isobutylmethylxanthine, have been proposed as "sunless" tanning agents, which act by modulating activity of the biochemical pathways involved in melanogenesis. Their proposed mechanism involves inhibition of cyclic-AMP phosphodiesterase, thus enhancing the biological activity of cyclic AMP in the pathways regulating melanogenesis. Methylxanthines can enhance the production of melanin in melanocytes, acting either alone or in combination with tanning stimulants like ultraviolet or solar radiation. However, methylxanthines are also known to exacerbate DNA damage caused by ultraviolet radiation, which has been attributed to an impairment of DNA repair or disruption of cell cycle control mechanisms (Kastan et al., *Cancer Research,* 51:6304–6311, 1991).

Compounds of the invention are useful for reducing the deleterious effect of methylxanthines on DNA damage caused by exposure of skin to ultraviolet or solar radiation. The compounds of the invention thus improve the safety of skin tanning products that contain methylxanthines as active ingredients. Compounds of the invention are applied either separately or in the same formulation as the methylxanthines.

Exfoliants

Cosmetics containing alpha-hydroxy acids (AHA) such as lactic acid, glycolic acid, citric acid, or malic acid are widely used. They have moisturizing and exfoliant properties. Products containing high concentrations of AHA are also used to produce more extreme "skin peels", in which the outer layers of the epidermis are removed, essentially by means of a chemical burn. New epidermis growing in is often softer and smoother than the skin layers that were removed. Beta-hydroxy acids like salicylic acid are also useful exfoliants. Retinoic acid is used for similar purposes through its exfoliant actions and through stimulation of epidermal cell turnover and alteration of epidermal metabolism.

Exfoliants are reported to reduce the sun-blocking capabilities of the stratum corneum, and furthermore increase the permeability of the skin to other agents. Thus, there is a need for use of UV protection in conjunction with AHA's, yet the increased skin permeability produced by AHA requires caution in the selection of sun protection agents, since absorbed sunscreen agents can produce photodynamic enhancement of DNA damage. The compounds of the invention are effective in reducing deleterious consequences of exposure to sunlight or ultraviolet radiation or other environmental mutagens in subjects using exfoliants, including but not limited to alpha-hydroxy acids, beta-hydroxy acids, and retinoids.

Nonsteroidal Anti-inflammatory Agents

Nonsteroidal anti-inflammatory agents are commonly used for treatment of arthritis and other anti-inflammatory agents. Moreover, some members of this class, e.g. diclofenac (2,6-dichloro-phenyl-amino-phenylacetate) are under investigation as topical agents for reducing some aspects of skin photodamage.

One of the prototypical members of this class of drugs, acetaminophen, inhibits DNA repair after damage caused by UV radiation by inhibiting the enzyme ribonucleotide reductase, which converts ribonucleoside diphosphates to deoxyribonucleoside diphosphates (Hongslo et al., *Mutagenesis,* 8:423–429, 1993). By supplying deoxyribonucleosides to skin, especially to areas of the skin that are generally exposed to sunlight, of patients receiving either oral or topical treatment with nonsteroidal anti-inflammatory agents, compositions of the invention overcome a deleterious consequence associated with this widely-used class of drugs.

Ornithine Decarboxylase Inhibitors

One consequence of UV irradiation of skin is an increase in cell proliferation rate and in the activity of enzymes necessary for cell proliferation, one of which is ornithine decarboxylase (ODC). Difluoromethylornithine (DFMO) is an inhibitor of ODC, which is necessary for polyamine synthesis, which in turn is necessary for DNA replication. DFMO is useful for reducing the incidence of skin cancer and precancerous actinic lesions. Inhibition of cell cycling after exposure to solar or UV radiation may give cells more time to repair DNA before mutagenic lesions are fixed by cell division, but cell cycle stasis also generally results in reduced levels of deoxyribonucleosides, which are necessary for repair of DNA damage. Deoxyribonucleosides are therefore useful in conjunction with DFMO and other antiproliferative agents which act via mechanisms not directly involving induced depletion or imbalance of deoxyribonucleotide pools. Deoxyribonucleosides of the invention are optionally incorporated into the same formulation as DFMO (or other inhibitors of skin cell proliferation that act through mechanisms other than impairment of DNA precursor synthesis), or are applied in a separate formulation.

Treatment of Skin During Exposure to Endogenous Nitric Oxide

Nitric oxide (NO) is a biologically active mediator released by endothelial cells, macrophages and other cell types, especially during inflammatory episodes. Nitric oxide is also an important mediator of erythema associated with UV exposure. Inhibitors of NO synthetase attenuate the increase in skin blood flow following exposure (Deliconstantinos et al., *J Cardiovasc Pharmacol* 20 Suppl 12:S63–5, 1992; Deliconstantinos et al., *Br J Pharmacol* 114(6):1257–65, 1995; Warren, *FASEB Journal,* 8(2):247–51, 1995).

Nitric oxide is a potent inhibitor of the enzyme ribonucleotide reductase (RR), which is the key enzyme for de novo synthesis of deoxyribonucleotides (Kwon et al., *J Exp Med* 174(4):761–7, 1991; LePoivre et al., *J Biol Chem* 269(34): 21891–7, 1994). The antiproliferative effects of nitric oxide are in part attributable to inhibition of ribonucleotide reductase. This can be beneficial in an inflammatory response to an infectious microorganism or a neoplasm, but is deleterious in cells in need of capability for DNA repair, e.g. skin exposed to inflammatory mediators elicited by UV exposure. The amounts of NO released from macrophages are sufficient to inhibit ribonucleotide reductase and thereby induce cytostasis in neighboring cells.

The best-known inhibitor of RR, hydroxyurea (HU), has structural similarities to N-omega-hydroxy-1-arginine, a physiological intermediate in NO production. Hydroxyurea can act as an NO-like nitrosating reactant (LePoivre et al., *J Biol Chem* 269(34):21891–7, 1994). Both NO and hydroxyurea inhibit RR by quenching a tyrosyl radical in the active site of the enzyme.

A discovery first disclosed herein is that NO sensitizes cells to UV-induced DNA damage via mechanisms that are reversible with exogenous deoxyribonucleosides (see Example 8). Moreover, NO by itself, in the absence of UV exposure, causes DNA damage that is prevented or reversed by compounds of the invention (Example 8).

The inflammatory response to UV exposure (which also plays an important role in UV-associated immunosuppression), via inhibition of ribonucleotide reductase by NO, exacerbates the mutagenic and cytotoxic effects of UV exposure. The subject invention provides a means for compensating for this deleterious effect of NO. Exogenous deoxyribonucleosides, which enter into DNA metabolism downstream of ribonucleotide reductase, compensate for reduced RR activity. NO, although deleterious in cells needing deoxyribonucleotides, has some beneficial effects in sun-exposed skin. Inhibitors of NO production also impair the healing of skin damaged by exposure to excessive UV radiation, i.e., UV doses that produce a sufficiently severe sunburn for wound healing processes to be called into action (Benrath et al., *Neurosci Lett*, 1995). Thus, NO is useful for tissue repair (probably by improving blood flow and perhaps also by stimulating growth factor release from macrophages or keratinocytes), but may simultaneously exacerbate UV-related damage to DNA by reducing cellular capacities for production of deoxyribonucleotides for DNA repair.

NO-mediated inhibition of RR provides a mechanism for a disproportionate increase in DNA damage without a corresponding increase in other symptoms of sun exposure during repeated exposure to strong sunlight. Topical application of the compounds and compositions of the invention provides a method for ameliorating this form of conditional hypersensitivity.

NO participates in skin inflammatory reactions that do not necessarily involve exposure to solar or ultraviolet radiation. NO, which is released from activated macrophages, is component of most inflammatory reactions. The compounds and methods of the invention provide a means of overcoming some deleterious effects of NO in inflammatory skin conditions, including but not limited to psoriasis, dermatitis, allergic dermatitis, eczema and acne. In these conditions, NO sensitizes some cell types to UV-induced DNA damage by inhibiting deoxyribonucleotide synthesis. Compounds and compositions of the invention ameliorate this deleterious consequence of combined UV exposure and inflammatory skin conditions. Since NO and other endogenous oxidants that cause DNA damage are present in inflammatory skin conditions like psoriasis or dermatitis even in the absence of significant exposure to UV radiation, the deoxyribonucleosides of the invention are useful for protecting genetic integrity of skin cells in inflammatory conditions. Compounds of the invention prevent or repair DNA damage caused by NO alone, without exposure to UV radiation (Example 8).

Ribonucleosides are also useful for treating inflammatory skin an mucosal conditions, in part by providing higher concentrations of the ribonucleotide substrates for ribonucleoside reductase. Ribonucleosides (or ribonucleoside esters) in this context are used in the same ways that deoxyribonucleosides, advantageously in topically-applied compositions, with ribonucleosides (or ribonucleoside esters) incorporated in concentrations ranging from 0.1 to 20 mg/ml, advantageously 1 to 5 mg/ml. Adenosine is particularly useful for treatment of inflammatory conditions.

Inhibition of DNA precursor synthesis by hydroxyurea leads to enhanced activity and leakage of hydrolytic lysosomal enzymes which participate in extracellular damage, e.g. in inflammatory skin conditions or photodamage (Malec et al., *Chem. Biol. Interact.*, 57:315–324, 1986). The compounds of the invention prevent this component of inflammatory tissue injury, especially when such inhibition of DNA precursor synthesis is mediated by endogenously-produced NO, which is functionally similar to hydroxyurea.

A further contribution to genomic damage is that exposure of cells to ultraviolet radiation results in the release of enzymes, including deoxyribonuclease, from lysosomes. Deoxyribonuclease II, which is present in lysosomes, is an endonuclease that can produce strand breaks in nuclear DNA following lysosome disruption. Leakage of enzymes from lysosomes also occurs in inflammatory conditions in general. The compounds and compositions of the invention are useful for preserving genomic integrity after chromosomal damage caused by deoxyribonuclease released from lysosomes in inflammatory skin conditions and after exposure of skin to solar or ultraviolet radiation.

By limiting some of the deleterious consequences of skin inflammation, compounds and compositions of the invention are useful as anti-inflammatory agents, and are optionally administered (either as separate compositions or, advantageously, in the same formulation) in conjunction with other topical or systemic anti-inflammatory agents including but not limited to corticosteroids like hydrocortisone and its congeners.

Similarly, compounds and compositions encompassed by the invention are useful for treatment of mucosal inflammatory conditions, including but not limited to inflammatory bowel disease, ulcerative colitis, or Crohn's disease, or mucositis anywhere in the gastrointestinal tract. The preferred mode of treatment is by topical administration, in this case via enema or suppository, for which purposes deoxyribonucleosides or other compounds of the invention are incorporated into suitable vehicles.

Treatment of Skin and Mucosal Tissues Exposed to Ionizing Radiation

Patients receiving therapeutic treatment (e.g. for cancer) with ionizing (X-Ray or gamma) radiation can suffer damage to skin overlying an internal tumor, leading to desquamation and poor healing. Compounds and compositions of the invention are useful for treating damage to skin and mucosal surfaces caused by intentional or accidental exposure to ionizing radiation. For treatment of skin, compositions of the invention are applied topically before or after radiation treatment. For treatment of mucosal surfaces, e.g. in the mouth, gastrointestinal tract, urethra or vagina, appropriate compositions of the invention are also applied topically. Suitable compositions for treatment of mucosal surfaces include gels, lotions, ointments, suppositories, orally-administered capsules, pills or dragees, or solutions.

E. Administration and Formulation of Compounds and Compositions of the Invention Compounds of the invention are formulated in pharmaceutically acceptable vehicles that deliver the compounds to the necessary cell populations in skin at concentrations adequate to accomplish the objectives of reducing mutation frequency and chance of developing cancer.

Compositions of the invention are applied before, during, or after exposure to sunlight or other mutagens. A lotion or hydrogel containing deoxyribonucleosides (0.1 to 10 mg/ml, advantageously 1 to 5 mg/ml) is applied to skin as a thin film. The composition should be applied within about 48 or 72 hours after exposure to damaging doses of sunlight or ultraviolet radiation, in order to provide support for DNA repair prior to the first cell divisions after irradiation, although application before, during, or within 12 hours after exposure to intense sunlight is advantageous. Compositions of the invention are also effective when applied before exposure to radiation or other mutagens, as long as the deoxyribonucleosides so provided, or their anabolites, are available to cells in need of their beneficial effects at the time of exposure to a mutagen. Advantageously, compositions of the invention are applied within about 12 hours before exposure of the skin to a solar radiation or other mutagens.

Compositions of the invention are advantageously applied as a daily-use skin treatment, once to several times per day, especially on sun-exposed parts of the body, or sites of inflammatory skin conditions. Exposure to solar radiation leading to skin photodamage and photoaging is generally a cumulative process, involving repeated exposure to sunlight, even daily, over a period of years. In this context, use of the compounds and compositions of the invention to prevent or treat photodamage to the skin involves treatment of existing lesions due to prior sun exposure, as well as prevention of, or attenuation of the severity of, damage due to present and future exposure to sunlight or other mutagens.

By improving repair of molecular damage to DNA as it occurs or before it is permanently established in the genome by cell division, or by preventing initial damage through energy scavenging, compositions of the invention prevent or delay the manifestation of deleterious consequences of radiation, free radicals, or chemical mutagens, such as grossly visible skin damage, photoaging, actinic keratoses, and skin cancer. Thus, compositions and methods of the invention reduce the rate of appearance and the incidence of signs of skin photodamage, especially when administered regularly, e.g. daily, or especially before, during, or after exposure to solar radiation.

In one embodiment of the invention, a composition containing deoxyribonucleosides is applied to skin prior to application of a sunscreen, as an alternative to use of formulations containing both conventional sunscreens and deoxyribonucleosides or related compounds of the invention.

For treatment of colon mucosal inflammation, e.g. inflammatory bowel disease, compositions of the invention are administered as a suppository or enema, approximately once per day according to clinical need. Volumes of 10 to 500 ml of a suitable enema composition containing deoxyribonucleosides are suitable for treatment of inflammatory bowel disease, e.g. ulcerative colitis or Crohn's disease. For treatment of mucositis in other parts of the gastrointestinal tract, such as the mouth, standard pharmaceutically acceptable vehicles for that route of administration are used, e.g. mouthwashes or adherent hydrocolloids.

F. Synthesis of the Compounds of the Invention

Deoxyribonucleosides, being constituents of DNA, are present in all living organisms, and can therefore in principle be extracted from a variety of sources. In practice, the most convenient biological sources at present are fish milt, which contains a relatively high concentration of DNA. Fish milt sacs are homogenized, and the DNA therein is partially purified and treated with deoxyribonucleases and phosphatases to degrade it to the level of nucleosides, which are then purified by chromatography and recrystallization.

Since mixtures of deoxyribonucleosides are used in some embodiments of the invention, purified deoxyribonucleosides are recombined in appropriate proportions. Alternatively, deoxyribonuclosides are not separated from each other during purification from other fish milt components (or other contaminants if the DNA is derived from other biological sources); appropropriate quantities of individual deoxyribonucleosides are added to such a mixture, if necessary, to adjust the relative proportions of deoxyribonucleosides.

Deoxyribonucleosides can also be synthesized chemically from simpler precursors.

Acyl derivatives of deoxyribonucleosides, as disclosed in U.S. Pat. No. 6,297,222, are useful for 1) providing sustained availability of deoxyribonucleosides due to gradual deacylation by nonspecific esterases in the skin, and 2) improved penetration through hydrophobic biological membranes or extracellular media, e.g. the intercellular lipids in the stratum corneum of the epidermis.

It will be obvious to the person skilled in the art that other methods of synthesis may be used to prepare the compounds of the invention.

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

EXAMPLE 1

Post-irradiation Topical Deoxyribonucleosides Improve DNA Repair in Mouse Skin after UVB Exposure The incidence of mutations in skin in response to ultraviolet radiation was determined using the "Big Blue" transgenic mouse test system. These mice carry approximately 40 copies per cell of a lambda phage shuttle vector containing a lacI gene as a target for mutagenesis, as well as the lacI promoter, the lac operator, and the αlacZ reporter gene.

Following exposure of the mice to ultraviolet radiation and treatment with compounds of the invention or vehicle, genomic DNA from skin samples is extracted and the shuttle vectors are packaged in lambda virus heads. The phage lambda viruses containing the shuttle vectors are plated on $E.\ coli$ with the color reagent X-Gal, which turns blue when enzymatically altered by galactosidase, the product of the αlacZ gene. Viruses containing nonmutated lacI genes produce white plaques; mutation of the lacI gene results in blue plaques. The mutation frequency is determined by counting the relative numbers of white and blue plaques.

Stratagene BigBlue™ transgenic mice (n=7/group) were shaved and then irradiated the next day with UVB radiation (85% of energy at 313 nm), 1.25 kJ/m2.

Deoxyribonucleosides ("dNsides"; 4 mg/ml each of deoxyadenosine, deoxycytidine, deoxyguanosine, and thymidine) or vehicle (propylene glycol) were applied topically 30 minutes after irradiation and again each day for 5 days.

Mice were sacrificed on day 5 after irradiation. DNA was extracted from dorsal (irradiated) and ventral (non-irradiated) skin, packaged into lambda phage and plated on $E.\ coli$ along with X-Gal. Colonies with mutations were blue. >200,000 colonies were counted in each group.

TABLE 1

Topical deoxyribonucleosides reduce mutation frequency in UV-irradiated skin

Spontaneous mutation frequency (nonirradiated skin):

Average: $4.5 \times 10^{-5}$

Mutation frequency in UVB-irradiated skin:

|  | Total | Increment due to UV |
|---|---|---|
| Control | $34.9 \times 10^{-5}$ | $30.4 \times 10^{-5}$ |
| dNsides | $7.8 \times 10^{-5}$ | $3.3 \times 10^{-5}$ |

As shown in Table 1, post-irradiation treatment with topical deoxyribonucleosides reduced the incidence of mutations caused by UV-B radiation by a factor of nearly 10 in this experiment ($30.4 \times 10^{-5}$ versus $3.3 \times 10^{-5}$)

EXAMPLE 2
Post-irradiation Treatment with Topical Deoxyribonucleosides Prevents Development of UV-induced Papillomas in v-Ha-ras Transgenic TG.AC Mice Example 1 demonstrated that post-irradiation topical treatment can reduce the frequency of UV-induced mutations in a reporter gene in "Big Blue" transgenic mice, through support and improvement of DNA repair processes. One of the consequences of reduced mutation frequency in response to a carcinogen like UV radiation should be a reduction of UV-induced tumorigenesis.

A strain of transgenic mice has been developed which is extremely sensitive to carcinogens. It permits rapid determination of carcinogenic potential of various chemical agents and other treatments. Normal mice require repeated exposure to ultraviolet radiation over a number of weeks in order to reliably develop skin tumors. In contrast, v-Ha-ras TG.AC transgenic mice can develop tumors rapidly after a single exposure, or small number of exposures to UV radiation.

In 9 mice exposed to UV-B radiation (0.3–1.25 kJ/m$^2$×3 q2d) and treated after irradiation with vehicle (propylene glycol), a total of 35 papillomas were found 4 weeks after exposure.

Among 7 mice exposed to the same doses of UV-B radiation and treated with deoxyribonucleosides (4 mg/ml of each major deoxyribonucleoside in propylene glycol) after irradiation, only 1 papilloma was observed (Table 2).

TABLE 2

Topical deoxyribonucleosides reduce UV-induced tumorigenesis

| | |
|---|---|
| Control: | 3.89 tumors/mouse |
| dNside-treated: | 0.14 tumors/mouse |

The beneficial effect of deoxyribonucleosides in reducing UV-induced tumorigenesis must be due to improvement of repair phenomena or cellular proofreading, or to inhibition of tumor promotion, and not to prevention of initial damage, since the deoxyribonucleosides were applied after irradiation. This observation indicates that deoxyribonucleoside treatment after (or presumably also during) exposure to UV-B radiation has important inhibitory effects on tumorigenesis, as a consequence of improved maintenance of genomic fidelity.

This antitumorigenic effect of topical deoxyribonucleosides even when applied after irradiation is particularly surprising in view of the reported efficacy of deoxyribonucleosides in accelerating wound healing (U.S. Pat. No. 5,246,708), since other growth factors known to accelerate wound healing, like platelet-derived growth factor (PDGF) or transforming growth factor beta (TGF-β), act as tumor promoters.

The antitumorigenic effect of deoxyribonucleosides in this experiment is also unexpected in view of the beneficial effect of deoxyribonucleosides on survival of cells in culture when the deoxyribonucleosides are applied after exposure of the cells to ultraviolet or ionizing radiation. Prevention of apoptosis of damaged cells would be expected to increase the likelihood of tumor development, as occurs in animals with defective p53-related mechanisms.

EXAMPLE 3
Low Concentrations of Oxybenzone Exacerbate UV-induced Damage to DNA Confluent human fibroblasts in T25 flasks were washed 3 times with HBSS (Hank's Balanced Salt Solution) and incubated with vehicle or with various concentrations of oxybenzone (OB) for 2 hours. Media was aspirated and cells were covered with a 1 mm layer of HBSS and irradiated from above with UV-B (50 J/m$^2$). The medium was aspirated and cells were incubated for three hours with 2 mM hydroxyurea. Medium was again aspirated, and cells were trypsinized with 0.25% trypsin/EDTA. Cells were centrifuged at 4° C., resuspended in 50 microliters of HBSS and incubated at room temperature with 200 microliters of 1N NaOH for 15 minutes. DNA damage (single strand breaks) was assessed by alkaline sucrose gradient centrifugation. "Nucleoid position" in the sucrose gradient is proportional to the number of DNA single strand breaks.

UV irradiation without oxybenzone results in a three to four-fold increase in the nucleoid position over baseline (Table 3). Oxybenzone at the higher concentrations tested, 20 and 200 micromolar, protected cellular DNA against damage from the UV irradiation, as the nucleoid position for these groups is close to that of non-irradiated cells. However, cells exposed to 2 micromolar OB display substantially more damage than cells irradiated with no OB at all; nucleoid position values are 10-fold greater than those of non-irradiated cells. Thus, oxybenzone strongly enhances DNA damage when present at low concentrations, whereas it protects cells at higher concentrations. In practice, even under conditions of proper sunscreen use, there will always be areas of skin exposed to low, potentially deleterious concentrations of sunscreen, either at the edge of a patch of applied sunscreen, or as an applied layer wears off over the course of a day.

TABLE 3

Low concentrations of oxybenzone enhance UV-induced DNA damage

| Group | Nucleoid Position (mm) |
|---|---|
| No UV | 3 |
| UV 50 J/m$^2$ | 11 |
| UV 50 J/m$^2$ + 2 μM OB | 32 |
| UV 50 J/m$^2$ + 20 μM OB | 4 |
| UV 50 J/m$^2$ + 200 μM OB | 3 |

EXAMPLE 4
Deoxribonucleosides Attenuate Photodynamic Enhancement of DNA Damage Caused by Oxybenzone Confluent human fibroblasts were exposed to 2 micromolar oxybenzone (OB), as in Example 3, prior to exposure to UV-B radiation (50 J/m$^2$). Different flasks of cells also were exposed to increasing concentrations of deoxyribonucleosides. Cells were processed for determination of nucleoid position in a sucrose density gradient, a measure of DNA single strand breaks.

As shown in Table 4, deoxyribonucleosides produce a dose-dependent reduction in the yield of DNA single strand breaks induced by UV exposure plus 2 μM OB. Deoxyribonucleosides at 2 μM slightly reduce DNA damage; at 200 micromolar, the deoxyribonucleosides almost completely abrogate the DNA damage.

TABLE 4

Deoxyribonucleosides attenuate photodynamic enhancement of DNA damage caused by UV plus oxybenzone

| Group | Nucleoid Position (mm) |
| --- | --- |
| UV + 2 µM OB | 56 |
| UV + 2 µM OB + 2 µM dNsides | 47 |
| UV + 2 µM OB + 20 µM dNsides | 23 |
| UV + 2 µM OB + 100 µM dNsides | 22 |
| UV + 2 µM OB + 200 µM dNsides | 7 |

EXAMPLE 5
Effect of Individual Versus Combined Deoxribonucleosides on Photodynamically-enhanced, UV-induced DNA Damage Human fibroblasts were prepared and treated as in Example 4, and the effects of individual deoxyribonucleosides on photodynamically enhanced DNA damage (2 µM oxybenzone) were determined. Individual deoxyribonucleosides were tested at concentrations of 20 µM, and the combination of all four deoxyribonucleosides contained thymidine, deoxycytidine, deoxyadenosine and deoxyguanosine at 20 µM each.

TABLE 5

Effect of individual versus combined deoxyribonucleosides on UV-induced DNA damage

| Group | DNA Strand Breaks (Breaks/47 MDa) |
| --- | --- |
| Control (no UV) | .0 |
| UV + vehicle | .325 |
| UV + thymidine | .13 |
| UV + deoxycytidine | .12 |
| UV + deoxyadenosine | .17 |
| UV + deoxyguanosine | .17 |
| UV + dNsides (20 µM each) | .01 |

As shown in Table 5, each of the individual deoxyribonucleosides attenuated DNA damage; the combination of all four deoxyribonucleosides was substantially more effective than any individual compound.

EXAMPLE 6
Sunscreen-induced Exacerbation of UV-induced Tumorigenesis and its Prevention with Deoxyribonucleosides A circular patch of commercial sunscreen (Coppertone SPF 8, which includes oxybenzone) was applied to the backs of TG.AC mice prior to exposure to 125 J/m² UV-B radiation.

Around the circular margin of the area that was covered with sunscreen during irradiation, 8 papillomas per mouse were present at 10 days. 3 tumors per mouse were observed in animals not treated with sunscreen. In mice exposed to UV radiation after application of the same commercial sunscreen to which deoxyribonucleosides had been added, no papillomas were elicited (Table 6).

TABLE 6

Deoxyribonucleosides attenuate tumorigenesis in in mice treated with UV plus sunscreen

| | |
| --- | --- |
| UV Radiation | 3 tumors/mouse |
| Sunscreen + UV radiation: | 8 tumors/mouse |
| Sunscreen containing dNsides + UV radiation: | 0 tumors/mouse |

Thus, at the margin of the applied patch of sunscreen where the sunscreen concentration diminishes in a rapid gradient toward zero, tumorigenic UV damage in fact appears to be enhanced rather than reduced by the sunscreen agents, leading to formation of more premalignant papillomas than on skin not treated with sunscreen at all.

Addition of deoxyribonucleosides to a commercial sunscreen abrogated the deleterious effect of the sunscreen on tumorigenesis.

EXAMPLE 7
Effect of Individual Deoxyribonucleosides Versus a Combination on UV-induced Tumorigenesis Thirty v-Ha-ras TG.AC mice aged twelve weeks were shaved and subjected to ultraviolet radiation, 1.25 kJ/m² on days 0, 6, 8 and 11, at a dose rate of 12.5 W/m2.

Mice were divided into groups of five animals each and treated, beginning 30 minutes after irradiation, with:

1. Vehicle (propylene glycol)
2. dNsides—Deoxyribonucleosides (4 mg/ml each of deoxyadenosine, deoxycytidine, deoxyguanosine, and thymidine)
3. dC—Deoxycytidine (4 mg/ml)
4. dG—Deoxyguanosine (4 mg/ml)
5. dA—Deoxyadenosine (4 mg/ml)
6. dT—Thymidine (4 mg/ml)

Animals were observed for 8 weeks, during which time the development of papillomas was observed.

TABLE 7

Effect of individual versus combined deoxyribonucleosides on UV-induced tumorigenesis

| Papillomas/mouse at the end of 8 weeks: | |
| --- | --- |
| Vehicle | 1.8 |
| dNsides | 0.0 |
| dC | 0.25 |
| dG | 1.0 |
| dA | 0.67 |
| dT | 1.6 |

As shown in Table 7, the mixture of all four deoxyribonucleosides provided the best activity in terms of prevention of tumor development. Deoxycytidine also provided protection; deoxyadenosine and deoxyguanosine were less protective but nonetheless had activity. Thymidine did not have significant protective actions.

EXAMPLE 8
Nitric Oxide Causes and Enhances DNA Damage by a Deoxyribonucleoside-reversible Mechanism Nitric oxide is a mediator of UV-induced erythema, and is also present in inflammatory skin conditions. NO is mutagenic, and may exacerbate UV-induced DNA damage, in part by inhibiting ribonucleotide reductase, the enzyme responsible for conversion of ribonucleotides to deoxyribonucleotides.

Human melanocytes were exposed to 160 µM DETA NONOate (Alexis Corporation, Cat #430-014-M005), a reagent which spontaneously produces nitric oxide when exposed to water. Cells were exposed to NO alone, or NO plus increasing doses of UV radiation (50 and 300 J/m²). Groups of cells were also exposed to deoxyribonucleosides of the invention before, or before and after, exposure to NO or NO+UV radiation; control groups were treated identically except for addition of deoxyribonucleosides.

DNA was extracted from cells and subjected to pulsed field gel electrophoresis to determine the incidence of DNA strand breaks.

As shown in Table 8, NO alone produced a significant incidence of DNA strand breaks, which were further increased by exposure to UV radiation. The deoxyribonucleosides of the invention strongly reduced the incidence of DNA strand breaks caused by NO, as well as those caused by the combination of NO plus UV radiation.

TABLE 8

Deoxyribonucleosides attenuate Nitric Oxide-induced DNA damage

| Groups | DNA Strand Breaks (breaks/105 MDa) |
| --- | --- |
| Control | 0.00 |
| NO | 0.13 |
| NO + UV 50 J/m$^2$ | 0.21 |
| NO + UV 300 J/m$^2$ | 0.51 |
| NO + dNsides before and after UV | 0.00 |
| NO + UV 50 J/m$^2$ + dNsides before/after UV | 0.03 |
| NO + UV 300 J/m$^2$ + dNsides before/after UV | 0.03 |
| NO + dNsides after UV | 0.06 |
| NO + UV 50 J/m$^2$ dNsides after UV | 0.06 |
| NO + UV 300 J/m$^2$ dNsides after UV | 0.03 |

What is claimed is:

1. A method of improving DNA repair in the skin or mucosa of a mammal exposed to a mutagen comprising administering to said mammal an effective DNA repair improving amount of an individual deoxyribonucleoside or of an individual deoxyribonucleotide; wherein said administration occurs during, after or up to 12 hours before said exposure.

2. A method as in claim 1 wherein said deoxyribonucleoside is administered topically.

3. A method as in claim 1 wherein said deoxyribonucleoside is selected from the group consisting of deoxycytidine, deoxyadenosine, deoxyguanosine, and thymidine.

4. A method as in claim 3 wherein said deoxyribonucleoside is deoxycytidine.

5. A method as in claim 3 wherein said deoxyribonucleoside is deoxyadenosine.

6. A method as in claim 3 wherein said deoxyribonucleoside is deoxyguanosine.

7. A method as in claim 3 wherein said deoxyribonucleoside is thymidine.

8. A method as in claim 3 wherein said deoxyribonucleoside is administered in a vehicle containing from 0.1 to 10 milligrams per milliliter of said deoxyribonucleoside.

9. A method as in claim 3 wherein said deoxyribonucleoside is administered in a vehicle containing from 1.0 to 5 milligrams per milliliter of said deoxyribonucleoside.

10. A method for reducing mutation frequency in skin of a mammal exposed to a mutagen comprising administering to said skin an effective mutation frequency reducing amount of a source of an individual deoxyribonucleoside wherein said source is selected from the group consisting of one deoxyribonucleoside in free form and the corresponding deoxyribonucleotide; and said administration occurs during, after or up to 12 hours before said exposure.

11. A method as in claim 10 wherein said mutagen is selected from the group consisting of ultraviolet or solar radiation, a chemical mutagen, a free radical, or ionizing radiation.

12. A method as in claim 10 wherein said source is the free deoxyribonucleoside.

13. A method as in claim 10 wherein said source is the corresponding deoxyribonucleotide.

14. A method as in claim 10 wherein said source is administered in a vehicle at a concentration of from 1.0 to 20 milligrams per milliliter.

15. A method as in claim 12 wherein said deoxyribonucleoside is free deoxycytidine.

16. A method as in claim 12 wherein said deoxyribonucleoside is free deoxyadenosine.

17. A method as in claim 12 wherein said deoxyribonucleoside is free deoxyguanosine.

18. A method as in claim 12 wherein said deoxyribonucleoside is free thymidine.

19. A method as in claim 12 wherein said deoxyribonucleoside is administered in a vehicle containing from 0.1 to 10 milligrams per milliliter of said deoxyribonucleoside.

20. A method as in claim 12 wherein said deoxyribonucleoside is administered in a vehicle containing from 1.0 to 5 milligrams per milliliter of said deoxyribonucleoside.

21. A method for reducing the rate of skin photoaging in the skin of a mammal exposed to ultraviolet or solar radiation comprising administering to the skin of said mammal an effective skin photoaging rate reducing amount of an individual deoxyribonucleoside; wherein said administration occurs during, after or up to 12 hours before said exposure.

22. A method as in claim 21 wherein said deoxyribonucleoside is deoxycytidine.

23. A method as in claim 21 wherein said deoxyribonucleoside is deoxyadenosine.

24. A method as in claim 21 wherein said deoxyribonucleoside is deoxyguanosine.

25. A method as in claim 21 wherein said deoxyribonucleoside is thymidine.

26. A method as in claim 21 wherein said deoxyribonucleoside is administered in a vehicle containing from 0.1 to 10 milligrams per milliliter of said deoxyribonucleoside.

27. A method as in claim 21 wherein said deoxyribonucleoside is administered in a vehicle containing from 1.0 to 5 milligrams per milliliter of said deoxyribonucleoside.

28. A method for protecting a mammal exposed to a mutagen against developing actinic keratoses, comprising administering to the skin of said mammal an effective actinic keratoses protecting amount of a source of an individual deoxyribonucleoside; wherein said source is selected from the group consisting of the deoxyribonucleoside in free form and the corresponding deoxyribonucleotide, and said administration occurs during, after or up to 12 hours before said exposure.

29. A method of reducing the DNA damage consequent to photosensitization or photodynamic sensitization on the skin of a mammal caused by an endogenous or exogenous photochemically active chromophore comprising administering to said skin an effective DNA damage reducing amount of an energy scavenging agent selected from the group consisting of a deoxyribonucleoside in free form and the corresponding deoxyribonucleotide, and said administration occurs during, after or up to 12 hours before said exposure to said chromophore.

30. A method as in claim 29 wherein said exogenous chromophore is a sunscreen agent.

31. A method as in claim 30 wherein said sunscreen agent is selected from the group consisting of avobenzone (t-butyl dimethoxydibenzoylmethane), oxybenzone (benzophenone-3), dioxybenzone (benzophenone-8), sulisobenzone (benzophenone-4,2-hydroxy-4-methoxybenzophenone-5-sulfonic acid), octocrylene (2-ethylhexyl-2-cyano-3,3-diphenylacrylate), octyl methoxycinnamate (2-ethylhexyl p-methoxycinnamate), octyl salicylate (2-ethylhexylsalicylate), homosalate (homomenthyl salicylate), trolamine salicylate (triethanolamine salicylate), phenylbenzimidazole sulfonic acid, PABA (para-aminobenzoic acid), roxadimate (ethyl 4-bis hydroxypropyl aminobenzoate), lisadimate (glyceryl PABA), Padimate O (octyldimethyl PABA), menthyl anthranilate, or Parsol 1789 (butyl methoxydibenzoylmethane).

32. A method as in claim 29 wherein said energy scavenging agent is administered in a vehicle containing said agent at a concentration from 0.1 to 20 mg/ml.

33. A method for reducing the mutagenesis consequent to exposure of a mutagen to the skin of a mammal comprising administering to said mammal an effective mutagenesis reducing amount of an individual deoxyribonucleoside or an individual deoxyribonucleotide.

34. A method as in claim 33 wherein said mutagen is solar or ultraviolet radiation.

35. A method as in claim 33 wherein said mutagen is ionizing radiation.

36. A method as in claim 33 wherein said mutagen is a free radical.

37. A method as in claim 33 wherein said deoxyribonucleoside is administered topically.

38. A method as in claim 33 wherein said deoxyribonucleoside is selected from the group consisting of deoxycytidine, deoxyadenosine, deoxyguanosine, and thymidine.

39. A method as in claim 33 wherein said deoxyribonucleoside is deoxycytidine.

40. A method as in claim 33 wherein said deoxyribonucleoside is deoxyadenosine.

41. A method as in claim 33 wherein said deoxyribonucleoside is deoxyguanosine.

42. A method as in claim 33 said deoxyribonucleoside is thymidine.

43. A method as in claim 33 wherein said deoxyribonucleoside is administered in a vehicle containing from 0.1 to 10 milligrams per milliliter of said deoxyribonucleoside.

44. A method as in claim 33 wherein said deoxyribonucleoside is administered in a vehicle containing from 1.0 to 5 milligrams per milliliter of said deoxyribonucleoside.

45. A method of reducing the deleterious consequences of exposure of skin to endogenously produced nitric oxide comprising administering to said skin an effective amount of a source of an individual deoxyribonucleoside; wherein said source is selected from the group consisting of the deoxyribonucleoside in free form and the corresponding deoxyribonucleotide, and said administration occurs during, after or up to 12 hours before said exposure and said deleterious consequences are selected from the group consisting of psoriasis, dermatitis, allergic dermatitis, eczema and acne.

46. A method as in claim 45 wherein said source is administered in a vehicle at a concentration of from 1.0 to 20 milligrams per milliliter.

47. A method as in claim 45 wherein said source is free deoxycytidine.

48. A method as in claim 45 wherein said source is free deoxyadenosine.

49. A method as in claim 45 wherein said source is free deoxyguanosine.

50. A method as in claim 45 wherein said source is free thymidine.

51. A method as in claim 45 wherein said deoxyribonucleoside is administered in a vehicle containing from 0.1 to 10 milligrams per milliliter of said deoxyribonucleoside.

52. A method as in claim 45 wherein said deoxyribonucleoside is administered in a vehicle containing from 1.0 to 5 milligrams per milliliter of said deoxyribonucleoside.

53. A method of treating skin inflammation in a mammal comprising administering to inflamed skin an effective skin inflammation treating amount of a source of an individual deoxyribonucleoside or ribonucleoside, wherein said deoxyribonucleoside source is the deoxyribonucleoside in free form or the corresponding deoxyribonucleotide and said ribonucleoside source is the ribonucleoside, the corresponding ribonucleotide or a corresponding acyl ribonucleoside.

54. A method as in claim 53 wherein said skin inflammation is selected from the group consisting of dermatitis, psoriasis, eczema, and acne.

55. A method as in claim 53 wherein said skin inflammation is due to exposure to solar or ultraviolet radiation.

56. A method as in claim 53 wherein said source is administered in a vehicle containing said source at a concentration from 0.1 to 20 mg/ml.

57. A method as in claim 53 wherein said source of deoxyribonucleoside is deoxycytidine.

58. A method as in claim 53 wherein said source of ribonucleoside is adenosine.

59. A method as in claim 58 wherein said adenosine is administered in a vehicle containing said adenosine at a concentration from 0.1 to 10 mg/ml.

60. A method of treating mucosal inflammation in a mammal comprising administering to said mucosal inflammation an effective mucosal treating amount of a source of an individual deoxyribonucleoside or ribonucleoside; wherein said deoxyribonucleoside source is the deoxyribonucleoside in free form or the corresponding deoxyribonucleotide and said ribonucleoside source is the ribonucleoside, the corresponding ribonucleotide or a corresponding acyl ribonucleoside.

61. A method as in claim 60 wherein said mucosal inflammation is selected from the group consisting of inflammatory bowel disease, ulcerative colitis, Crohn's disease, stomatitis or mucositis.

62. A method as in claim 60 wherein said source is administered in a vehicle containing said source at a concentration from 0.1 to 20 mg/ml.

63. A method as in claim 60 wherein said source of at least one deoxyribonucleoside is deoxycytidine.

64. A method for reducing the rate of development of skin photodamage in a mammal exposed to solar or ultraviolet radiation comprising administering to the skin of said mammal an effective skin photodamage rate reducing amount of a source of an individual deoxyribonucleoside wherein said source is administered such that said deoxyribonucleoside is present on skin of said mammal during or after exposure to said radiation in an amount sufficient to reduce the deleterious consequences of said exposure; wherein said source is selected from the group consisting of the deoxyribonucleoside in free form and the corresponding deoxyribonucleotide.

65. A method as in claim 64 wherein said source is the free deoxyribonucleoside.

66. A method as in claim 64 wherein said source is the corresponding deoxyribonucleotide.

67. A method of reducing the rate of development of skin photodamage in a mammal due to exposure to solar or ultraviolet radiation comprising topically administering an effective skin photodamage rate reducing amount of a composition comprising a sunscreen agent and an energy scavenging agent; wherein said energy scavenging agent is selected from the group consisting of an individual deoxyribonucleoside in free form or the corresponding ribonucleoside, ribonucleotide, deoxyribonucleotide, or a corresponding acyl ribonucleoside.

* * * * *